United States Patent [19]

Creuzet et al.

[11] Patent Number: 4,499,090

[45] Date of Patent: Feb. 12, 1985

[54] N-(5-AMINOMETHYL-2-OXAZOLIN-2-YL)-N'-PHENYLUREAS, COMPOSITIONS AND USE

[75] Inventors: Marie-Hélène Creuzet, Bordeaux; Claude Feniou, Pessac; Christian Jarry, Artigues Près Bordeaux; Gisèle Prat, Talence; Henri Pontagnier, Pessac, all of France

[73] Assignee: Societe Cortial, S.A., Paris, France

[21] Appl. No.: 539,285

[22] Filed: Oct. 5, 1983

[30] Foreign Application Priority Data

Oct. 5, 1982 [FR] France .................................. 82 16783
Aug. 4, 1983 [FR] France .................................. 83 13013

[51] Int. Cl.³ .................. C07D 263/28; C07D 295/14; A61K 31/42; A61K 31/535

[52] U.S. Cl. ...................... 514/210; 544/137; 544/360; 544/369; 546/146; 546/193; 546/209; 546/281; 548/233; 514/211; 514/212; 514/235; 514/318; 514/325; 514/340; 514/377

[58] Field of Search ................ 544/137, 360, 369; 546/146, 193, 209, 281; 548/233; 424/248.54, 250, 258, 263, 267, 272

[56] References Cited

U.S. PATENT DOCUMENTS 3,299,089 1/1967 Zimmermann et al. ............. 548/233

*Primary Examiner*—Robert W. Ramsuer

*Attorney, Agent, or Firm*—Oblon, Fisher, Spivak, McClelland & Maier

[57] ABSTRACT

This invention relates to new N-(5-aminomethyl-2-oxazoline-2-yl)-N'-phenylureas, the method for producing them and their application in therapy, particularly in treating convulsions, rhythm troubles, ulcerous disorders or inflammatory or edematous conditions.

The products of this invention have the general formula:

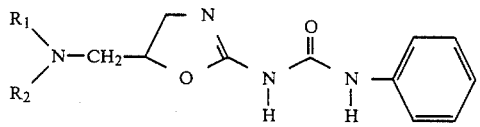

wherein $R_1$ and $R_2$ independently represent an alkyl radical of $C_1$ to $C_4$, or a carbocyclic alkyl radical having 3 or less rings, or a carbocyclic radical having 3 or less rings; $R_1$ and $R_2$ can form, with the nitrogen atom to which they are attached, a 4 to 7 member heterocycle containing 1 or 2 nitrogen atoms and 1 or 0 oxygen atoms, said heterocycle can be substituted by R with R being an alkyl radical of $C_1$ to $C_4$, allyl, benzyl, pyridyl, phenyl substituted or not by one or more substituents such as halogen, trihalomethyl, alkyl of $C_1$ to $C_4$, hydroxy, or alkoxy having a $C_1$ to $C_4$ alkyl radical.

10 Claims, No Drawings

N-(5-AMINOMETHYL-2-OXAZOLIN-2-YL)-N'-PHENYLUREAS, COMPOSITIONS AND USE

BACKGROUND OF THE INVENTION

1. Field of the Invention

This invention relates to new N-(5-aminomethyl-2-oxazolin-2-yl)-N'-phenylureas, the method for producing them and their therapeutic application.

2. Description of the Prior Art

2-Amino-2-oxazolines are already known. Thus, 2-amino-5-phenyl-2-oxazoline

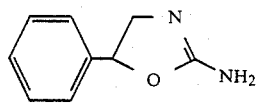

was patented by MacNeil Laboratories Incorporated in France under No 2448M for its properties of stimulation of the central nervous system and its anorexigenic activity. 2-Amino-5-(3,4-dichlorophenoxymethyl)-2-oxazoline was tested by A. H. Abdallah and coll. for its cardiovascular and anorexigenic activity (Toxicol. appl. Pharmacol., 1973, 26, 513–22; 1973, 25, 344–53) and was patented by the Dow Chemical Company in the United States under No. 3,637,726 on Apr. 9, 1970 for its antimicrobial activity.

A urea substitution derivative of formula

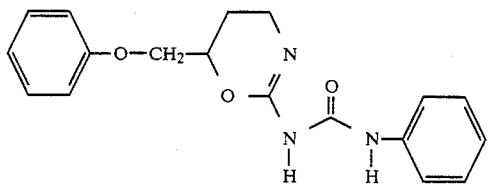

described by the Delalande company in French Pat. No. 7311985 is also known.

SUMMARY OF THE INVENTION

The products of this invention are distinguished from already known derivatives by the presence of an aminomethyl substituent in the 5 position of the oxazoline ring. They exhibit pharmacological properties making possible their application in therapy, particularly in treating convulsions, rhythm troubles, ulcerous disorders or inflammatory or edematous conditions.

The products of this invention have the general formula:

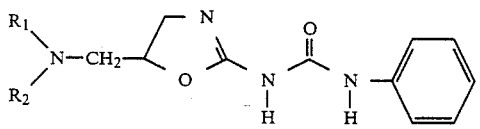

with $R_1$, $R_2$, identical or different, =alkyl (such as $CH_3$, $C_2H_5$, $C_3H_7$, $C_4H_9$) or arylalkyl (such as benzyl); $R_1$ and $R_2$ can form, with the nitrogen atom to which they are attached, a heterocycle such as piperidine, pyrrolidine, morpholine, tetrahydroisoquinoline, or else piperidine or piperazine substituted by R with R=lower alkyl of $C_1$ to $C_4$, allyl, benzyl, pyridyl, phenyl substituted or not by one or more substituents such as halogen (for example, chloro, fluoro, bromo), trifluoromethyl, methyl, methoxy, hydroxy.

DESCRIPTION OF THE PREFERRED EMBODIMENTS

The products of this invention are prepared in a general manner by reaction between an 2-amino-5-aminomethyl-2-oxazoline and phenyl isocyanate in a solvent such as benzene at the boiling point of the solvent.

The invention will be further illustrated by certain examples and references which are provided for purposes of illustration only and are not intended to limit the present invention.

EXAMPLE 1

N-(5-diethylaminomethyl-2-oxazolin-2-yl)-N'-phenylurea. Product of formula I with $R_1=R_2=C_2H_2$.

17.1 g of 2-amino-5-diethylaminomethyl-2-oxazoline, previously dissolved in 150 cc of benzene, are introduced in a reactor equipped with cooling, a dropping funnel and stirring. The mixture is brought to boiling and 11.9 g of phenyl isocyanate are added drop by drop. Heating is continued for two hours after the end of addition of phenyl isocyanate. During cooling, a precipitate is formed which is drained and recrystallized in $CCl_4$. Yield 92%. Melting point=148° C. NMR in DMSO($d_6$) (chemical shifts are expressed in ppm in relation to TMS taken as the internal standard): 0.9 ppm, 6 protons, triplet ($CH_3$); 2.3–2.8 ppm, 6 protons, complex mass, ($CH_2N$); 3.2–4.0 ppm, 2 protons, complex mass (H in 4 of oxazoline ring); 4.5–5.0 ppm, 1 proton, complex mass (H in 4 of oxazoline ring); 6.7–7.8 ppm, 5 protons, complex mass, (aromatic protons); 8.7 and 9.3 ppm, 2 protons, domes (NHCONH).

EXAMPLE 2

N-Phenyl-N'-(5-piperidinomethyl-2-oxazoline-2-yl)urea; formula I with $R_1$ and $R_2$ together=—$CH_2$—$CH_2$—$CH_2$—$CH_2$—$CH_2$—.

This product is prepared by the technique described in Example 1. Melting point 170° C. NMR in $CDCl_3$: 1.2–1.8 ppm, 6 protons, complex mass ($CH_2C$); 2.2–2.8 ppm, 6 protons, complex mass ($CH_2N$); 3.3–4.0 ppm, 2 protons, complex mass (H in 4 oxazoline ring); 4.5–5.1 ppm, 1 proton, complex mass (H in 5 of oxazoline ring); 6.8–7.7 ppm, 5 protons, complex mass (aromatic protons); 8.2 and 8.8 ppm, 2 protons, domes NHCONH).

EXAMPLE 3

N-phenyl-N'-(1,2,3,4-tetrahydro-5-isoquinolinemethyl-2-oxazolin-2-yl)urea; formula I with $R_1$ and $R_2$ together=

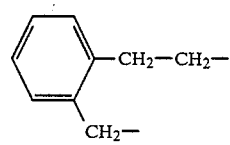

This product is prepared by the technique described in Example 1. Melting point=179° C.

NMR in DMSO(d₆) ( 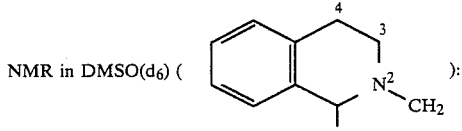 ):

2.6–3.1 ppm, 6 protons, complex mass (H in 3,4 of isoquinoline ring+CH₂ in alpha); 3.2–4.0 ppm, 4 protons, complex mass (H in 1 of isoquinoline ring+H in 4 of oxazoline ring); 4.5–5.1 ppm, proton, complex mass (H in 5 of oxazoline ring); 6.6–7.7 ppm, 9 protons, complex mass (aromatic H); 8.7–9.3 ppm, 2 protons, domes (NHCONH).

EXAMPLE 4

N-(5-(4-methylpiperazinylmethyl)-2-oxazolin-2-yl)-N'-phenylurea. Product of formula I with

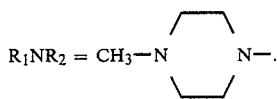

$R_1NR_2 = CH_3-N\underset{\_\_\_}{\overset{\frown}{\phantom{X}}}N-$.

This product is prepared by the technique described in Example 1.

Melting point 150° C. (Kofler stand).

NMR spectrum in DMSO(d₆), (chemical shifts expressed in ppm in relation to TMS taken as internal standard); 2.0–2.8 ppm, 13 protons, complex mass, methylpiperazinylmethyl of which CH₃ at 2.1 ppm; 3.2–4.0 ppm, 2 protons, complex mass, CH₂ of oxazoline ring; 4.5–5.1 ppm, 1 proton, multiplet, CHO, 6.7–7.8 ppm, 5 protons, complex mass, aromatic protons; 8.7 and 9.3 ppm, 2 protons, domes 2 NH, interchangeable with D₂O.

EXAMPLE 5

N-(5-benzylpiperidinylmethyl)-2-oxazolin-2-yl)-N'-phenylurea. Product of formula I with

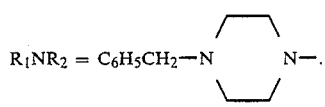

$R_1NR_2 = C_6H_5CH_2-N\underset{\_\_\_}{\overset{\frown}{\phantom{X}}}N-$.

This product is prepared as in Example 1.

Melting point 181° C. (Kofler stand).

NMR spectrum in DMSO(d₆): 0.9–4.0 ppm, 15 protons, complex mass, CH₂ and CH; 4.5–5.0 ppm, 1 proton, multiplet; CHO; 6.7–7.8 ppm, 10 protons, complex mass, aromatic protons, 8.7 and 9.3 ppm, 2 protons, domes, 2 NH, interchangeable with D₂O.

EXAMPLE 6

N-(5-benzylpiperazinylmethyl)-2-oxazolin-2-yl)-N'-phenylurea. Product of formula I with

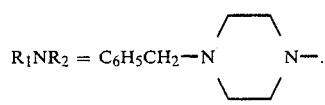

$R_1NR_2 = C_6H_5CH_2-N\underset{\_\_\_}{\overset{\frown}{\phantom{X}}}N-$.

This product is prepared as in Example 1.

Melting point 184° C. (Kofler stand).

NMR spectrum in DMSO(d₆): 2.2–2.8 ppm, 10 protons, complex mass, CH₂ piperazinylmethyl; 3.2–4.0 ppm, 4 protons, complex mass, CH₂ of oxazoline ring=benzylic CH₂; 4.5–5.1 ppm, 1 proton, multiplet, CHO; 6.7–7.8 ppm, 10 protons, complex mass, aromatic protons; 8.8 and 9.3 ppm, 2 protons, domes, 2 NH; interchangeable with D₂O.

The toxicopharmacological properties of the products of this invention are set forth below.

The toxicity was determined in mice for various ways of administration. Thus, the products of Examples 1, 2 and 3 did not cause any mortality when they were administered orally at 300 mg/kg or intraperitoneally at 200 mg/kg.

When administered intraperitoneally in a dose of 100 mg/kg the products of Examples 1 and 2 prevented the appearance of arrhythmias in mice subjected to chloroform anesthesia.

When administered intraperitoneally in a dose of 80 mg/kg the product of Example 3 caused an inhibition of convulsions induced by an injection of 0.5 mg/kg of bicuculline 30 minutes later. The product of Example 3 does not act on the GABA transaminase because it no longer inhibits convulsions induced by a second administration of bicuculline 5 hours later. its activity therefore is the direct gabergic type.

In a concentration of 100 microg/ml, the product of Example 1 inhibited at more than 50% the chronotropic effect induced by 5 microg/ml of histamine on the right auricle of a guinea pig beating spontaneously.

Administered orally in a dose of 200 mg/kg, the product of Example 1 caused an inhibition of 51% of edema of a rat's foot induced by carrageenan.

Considering their pharmacological activities, the products of this invention can be used in human and veterinary therapy. When associated with the usual excipients, they can be used, for example, to treat cardiac rhythm troubles, generalized and localized epilepsies, febrile convulsions in children, ulcerous disorders, inflammatory and edematous conditions.

They will be administered, for example, orally in the form of dragees, tablets, syrup, ampules, rectally as suppositories, intramuscularly or intravenously or topically as ointments or gels; the doses administered will vary, depending on the indication and patient, from 1 to 100 mg/d in 2 to 6 doses orally, from 1 to 100 mg/d in 1 or 2 doses rectally, from 0.5 to 50 mg by parenteral injection.

What is claimed as new and is intended to be secured by Letters Patent is:

1. A compound having the general formula:

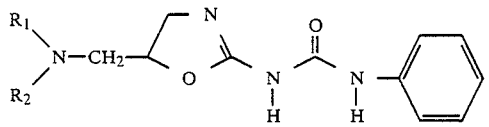

wherein $R_1$ and $R_2$ independently represent an alkyl radical of $C_1$ to $C_4$, or a carbocyclic alkyl radical having less than 4 rings, or a carbocyclic radical having less than 4 rings; $R_1$ and $R_2$ can form, with the nitrogen atom to which they are attached, a 4 to 7 member heterocycle containing 1 or 2 nitrogen atoms and 1 or 0 oxygen atoms, said heterocycle can be substituted by R with R being an alkyl radical of $C_1$ to $C_4$, allyl, benzyl, pyridyl, phenyl substituted or not with one or more substituents such as halogen, trihalomethyl, alkyl of $C_1$ to $C_4$, hydroxy, or alkoxy having a $C_1$ to $C_4$ alkyl radical.

2. A compound described in claim 1, wherein $R_1$ and $R_2$ are independently chosen from the group consisting of methyl, ethyl, n-propyl, iso-propyl, n-butyl, sec-butyl, iso-butyl, tert-butyl, benzyl, and phenyl.

3. A compound described in claim 1, wherein said heterocycle formed by $R_1$ and $R_2$ is chosen from the group consisting of piperidine, pyrrolidine, morpholine, tetrahydroisoquinoline, and piperazine.

4. A pharmaceutical or veterinary composition characterized in that it comprises as active principle a product as in claim 1 in association with a pharmaceutical vehicle or a suitable excipient.

5. A method for treating cardiac rhythm troubles which comprises administration of an effective amount of a compound of claim 1.

6. A method for treating epilepsy which comprises administration of an effective amount of a compound of claim 1.

7. A method for treating convulsions which comprises administration of an effective amount of a compound of claim 1.

8. A method for treating ulcerous disorders which comprises administration of an effective amount of a compound of claim 1.

9. A method for treating inflammatory conditions which comprises administration of an effective amount of a compound of claim 1.

10. A method for treating edematous conditions which comprises administration of an effective amount of a compound of claim 1.

* * * * *